United States Patent [19]

Rosenstatter

[11] Patent Number: 5,332,389

[45] Date of Patent: Jul. 26, 1994

[54] DENTAL HANDPIECE CONNECTING PORTION RECEIVING ALTERNATIVE ILLUMINATION MEMBERS

[75] Inventor: Otto Rosenstatter, Seeham, Austria

[73] Assignee: Imtec Innovative Medizintechnik Gesellschaft m.b.H., Salzburg, Austria

[21] Appl. No.: 952,267

[22] Filed: Sep. 28, 1992

[30] Foreign Application Priority Data

Dec. 6, 1991 [DE] Fed. Rep. of Germany ... 9115186[U]

[51] Int. Cl.⁵ .................. A61C 1/00; A61C 3/00; A61C 1/08
[52] U.S. Cl. ...................... 433/29; 433/126
[58] Field of Search ............ 433/29, 114, 126

[56] References Cited

U.S. PATENT DOCUMENTS

| 4,600,384 | 7/1986 | Olsen | 433/29 |
| 4,669,982 | 6/1987 | Fleer | 433/29 |
| 4,681,540 | 7/1987 | Landgraf et al. | 433/126 |
| 5,033,960 | 7/1991 | Heil | 433/29 |
| 5,057,015 | 10/1991 | Fleer | 433/126 |
| 5,074,785 | 12/1991 | Malata, Jr. | 433/29 |

FOREIGN PATENT DOCUMENTS 3104239  8/1982  Fed. Rep. of Germany.

Primary Examiner—Gene Mancene
Assistant Examiner—Cindy A. Cherichetti
Attorney, Agent, or Firm—Wenderoth, Lind & Ponack

[57] ABSTRACT

A dental handpiece includes a handle portion having at a first end thereof a holder for a driven tool and which at a second end thereof is rotatably connected to a connecting portion which provides connection to a supply hose for supply media. Light supplied to the region of the tool is provided from an incandescent lamp arranged in a recess in the connecting portion. The recess may accommodate the incandescent lamp or a light guide and is arranged at an end of the connecting portion to be directed toward the hose and opens at such end.

12 Claims, 4 Drawing Sheets

DENTAL HANDPIECE CONNECTING PORTION RECEIVING ALTERNATIVE ILLUMINATION MEMBERS

BACKGROUND OF THE INVENTION

The present invention relates to a dental handpiece including a handle portion which at one end has a holder for a driven tool and which at the other end is rotatably connected to a connecting portion which provides connection to a supply hose for supply media. Light issuing in the region of the tool may be produced by an incandescent lamp arranged in a recess in the connecting portion.

In a handpiece of such type, the function of the connecting portion is to provide connection of a given kind of supply hose to a series of different handle portions. Supply hoses of different configurations each have associated therewith their own connection portions which are permanently connected to the supply hose.

In a known type of connecting portion (see DE-C-31 04 239) the incandescent lamp which serves to produce the light is disposed in the center of the end of the connecting portion which is directed towards the tool. That has the advantage that only an electric line and not an optical line has to be passed through the connecting portion. If, on the other hand, the supply hose provides light, then a connecting portion of a substantially different structure must be used for that purpose.

SUMMARY OF THE INVENTION

The object of the present invention is to provide a connecting portion which with minor modifications can be selectively used for supply hoses which provide either light or an electrical voltage for supplying an incandescent lamp.

To attain that object, in accordance with the invention it is provided that a recess for receiving the incandescent lamp is arranged at a hose end of the connecting portion and opens on such end.

A particularly simple structural configuration is provided if contact pins of the incandescent lamp pass through a closure plate, which is towards the hose, of the connecting portion.

The connecting of the connecting portion to the handle portion is particularly simple when the light issues in known manner centrally from the connecting portion. Therefore, with an eccentric arrangement of the incandescent lamp, it is desirable if there is provided a mirror arrangement which provides for parallel displacement of light coming from the incandescent lamp, so that it issues axially from the connecting portion.

If light instead of electrical voltage is provided by the supply hose, then for the purposes of conversion of the connecting portion according to the invention, it is sufficient to use a glass rod or bar instead of the incandescent lamp. Most parts of the connecting portion are therefore identical for both types of supply hoses.

BRIEF DESCRIPTION OF THE DRAWINGS

Further details of the invention are described hereinafter with reference to the accompanying drawings, in which.

DETAILED DESCRIPTION OF THE INVENTION

Figure 1:
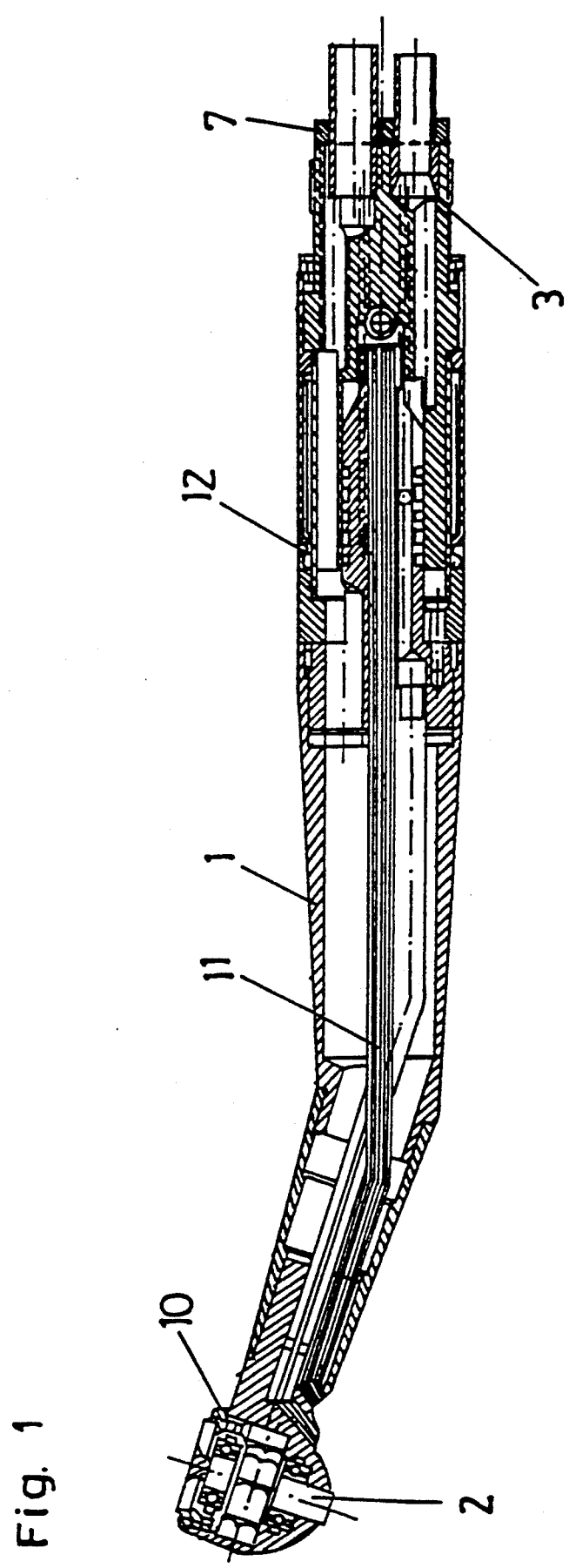
FIG. 1 is a longitudinal section through a dental handpiece.
Figure 2:
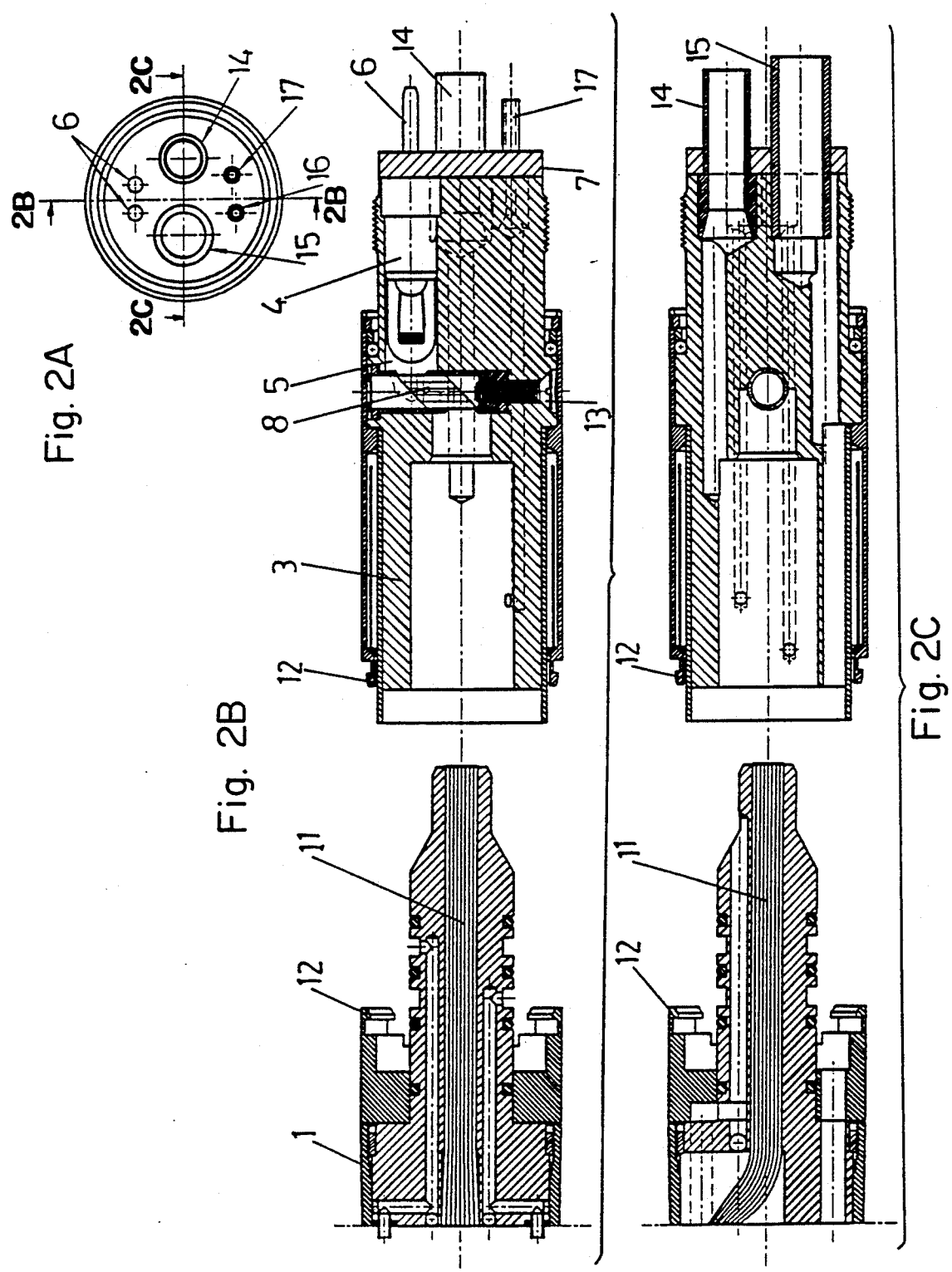
FIG. 2A is an end view of a connecting portion of the dental handpiece of FIG. 1 and equipped with an incandescent lamp.
FIG. 2B is a section taken along line 2B—2B of FIG. 2A.
FIG. 2C is a section taken along line 2C—2C of FIG. 2A.

The dental handpiece shown in FIG. 1 comprises a handle member or portion 1 with a holder 2 for a tool (not shown) which is drivable by way of an air turbine 10. A light conduit 11 passes through the handle portion 2. Light issuing from the conduit 11 is directed toward the region of the tool.

In order to be able to operate with different types of supply hoses, the handle portion 1 is to be connected in each case to a suitable connecting member or portion 3 which makes the connection to the respective supply hose (not shown). The connecting portion 3 is connected rotatably relative to the handle portion 1 by way of an easily releasable quick-action coupling 12.

In accordance with the invention, a recess 5, within which can be positioned an incandescent light bulb or lamp 4 for producing light which is passed to the light conduit 11, is disposed in an end of the connecting portion 3 which is remote from the handle portion 1. Recess 5 opens away from handle portion 1, i.e. toward the supply hose (not shown). Contact pins 6 of the incandescent lamp 4 pass through openings in a closure plate 7 of the connecting portion 3 and can therefore be inserted directly into an end part (not shown) of a supply hose. The same applies for connections 14, 15, 16 and 17 for the supply to or from the dental handpiece of drive air, return air, treatment air and water.

While the passage of air and water through the rotatable connection between the handle portion 1 and the connecting portion 3 is provided in conventional manner, the arrangement according to the invention of the incandescent lamp 4 at the end of the connecting portion 3 which is towards the hose is novel. In order to provide for a central egress of the light beam to the end of the light conduit 11, in spite of the eccentric arrangement of the incandescent lamp 4, provided adjoining the incandescent lamp 4 is a mirror arrangement 8 in the form of a prism which can be removed after loosening a screw 13.

Figure 3:
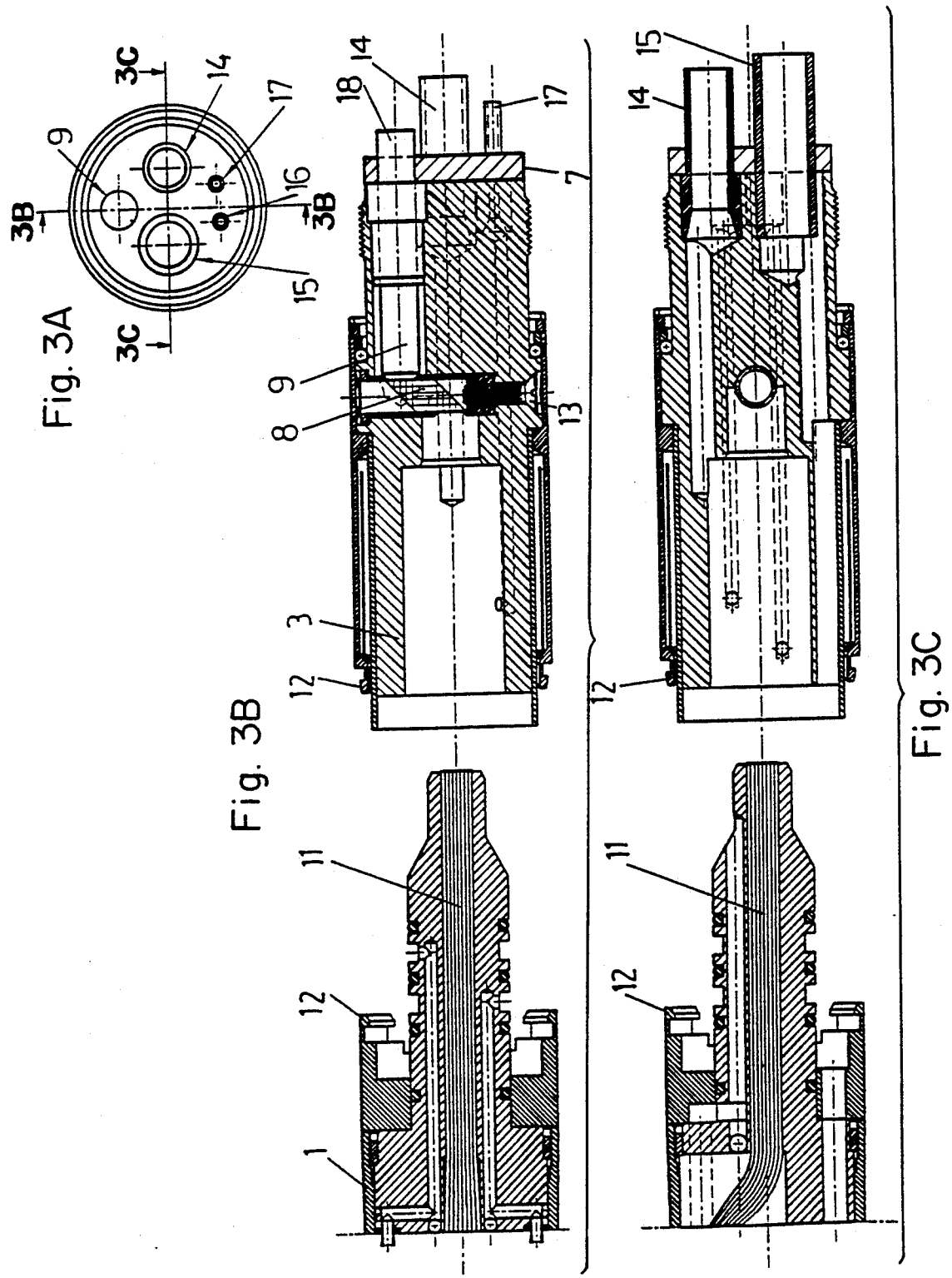
FIGS. 3A-3C are views similar to FIGS. 2A-2C, respectively, but wherein the dental handpiece is not equipped with an incandescent lamp.
Figure 4:
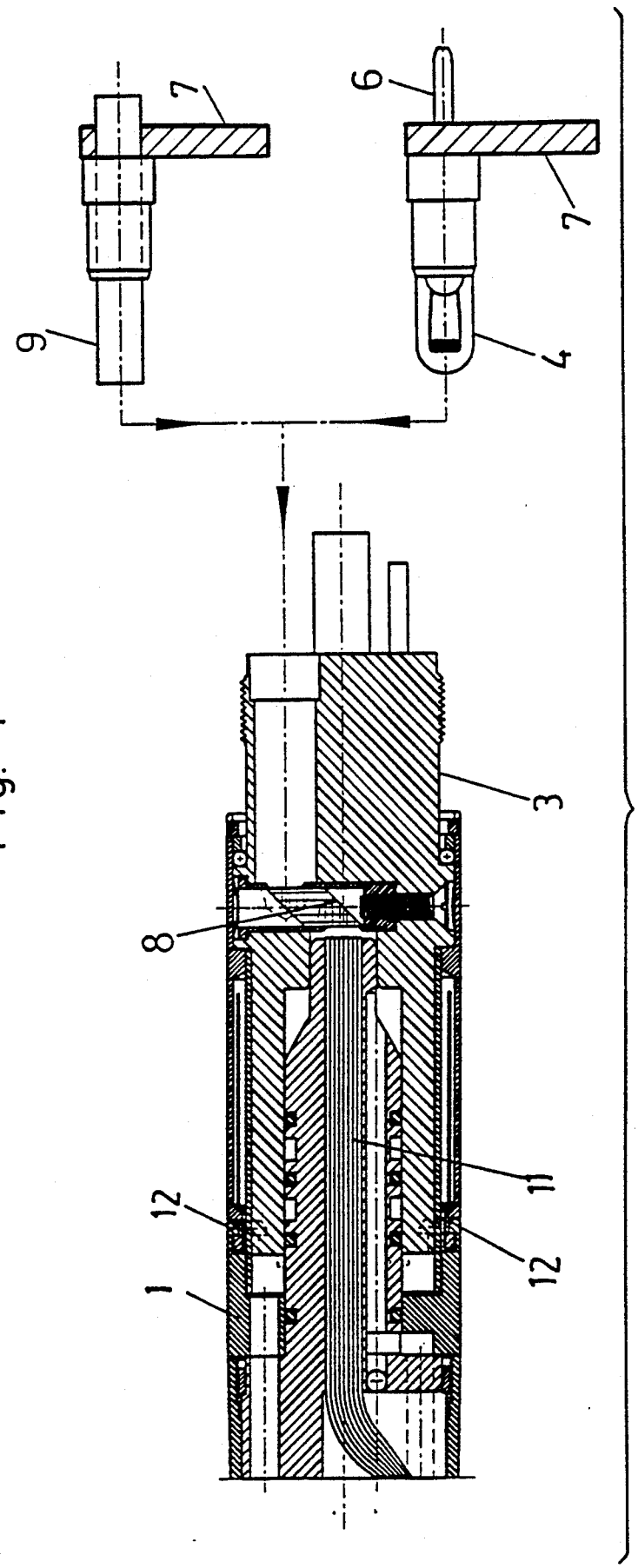
FIG. 4 is a longitudinal section illustrating change between the arrangement of FIGS. 2A-2C and the arrangement of FIGS. 3A-3C.

As can be seen from FIGS. 3A-3B, the connecting portion 3 remains almost unchanged if the provision of an incandescent lamp 4 is superfluous due to the supply hose already delivering a light beam to the connecting portion 3. Instead of the incandescent lamp 4, in this case for example use is made of a glass bar or rod 9 or other passive light guide device which merely serves to transmit light supplied thereto to conduit 11 via arrangement 8. A portion 18 of light guide 9 extends through an opening in closure plate 7 for optical connection to light supplied from the supply hose. As can be seen from FIG. 4, the manufacturer, for producing the desired connecting portion 3, only needs to make a choice between a glass rod or bar 9 or an incandescent lamp 4, whereas the remainder of the connecting portion 3 remains unchanged.

I claim:

1. A dental handpiece comprising:
    a handle portion having at a first end thereof a holder for a driven tool and a second end;
    a connecting portion having a first end rotatably connected to said second end of said handle portion and a second end to be connected to a supply hose for supply of media to said dental handpiece;
    a recess formed in said second end of said connecting portion, said recess having an open end directed in a direction to be toward the supply hose; and
    an illumination member, to enable light to be supplied to the region of the tool, removably positioned in said recess and insertable into and removable therefrom through said open end thereof.

2. A dental handpiece as claimed in claim 1, wherein said illumination member comprises an incandescent lamp.

3. A dental handpiece as claimed in claim 2, further comprising a closure plate attached to said second end of said connecting portion and closing said open end of said recess, and said incandescent lamp having contact pins passing through said closure plate to be connected to an electrical source of the supply hose.

4. A dental handpiece as claimed in claim 1, wherein said illumination member comprises a light guide.

5. A dental handpiece as claimed in claim 4, further comprising a closure plate attached to said second end of said connecting portion and closing said open end of said recess, and said light guide extending through said closure plate to be connected to a light source of the supply hose.

6. A dental handpiece as claimed in claim 1, wherein said recess is located eccentrically of an axial center of said connecting portion, and further comprising a mirror arrangement mounted in said connecting portion to parallelly displace light from said illumination member so that such light issues axially from said first end of said connecting portion.

7. A dental handpiece as claimed in claim 6, further comprising a light conduit mounted within said handle portion and having a first end directed to the tool region and a second end positioned to receive light issuing axially from said first end of said connecting portion.

8. A dental handpiece connecting portion for use in connecting a handle portion of a dental handpiece to a supply hose for supply of media to the dental handpiece, said connecting portion comprising:
    a first end to be rotatably connected to the handle portion and a second end to be connected to the supply hose; and
    a recess formed in said second end of said connecting portion, said recess having an open end directed in a direction to be toward the supply hose, such that an illumination member may be removably positioned in said recess and be inserted into and removed therefrom through said open end thereof.

9. A connecting portion as claimed in claim 8, further comprising a closure plate attached to said second end and closing said open end of said recess.

10. A connecting portion as claimed in claim 9, wherein said closure plate has therein openings to receive contact pins of an incandescent lamp to be provided as an illumination member.

11. A connecting portion as claimed in claim 9, wherein said closure plate has therethrough an opening to receive a light guide to be provided as an illumination member.

12. A connecting portion as claimed in claim 8, wherein said recess is located eccentrically of an axial center of said connecting portion, and further comprising a mirror arrangement mounted in said connecting portion to parallelly displace light from said illumination member so that such light issues axially from said first end of said connecting portion.

* * * * *